(12) United States Patent
Sumi et al.

(10) Patent No.: US 11,045,425 B2
(45) Date of Patent: Jun. 29, 2021

(54) METHOD OF ENCAPSULATING PANCREATIC ISLET CELLS INTRODUCED TO SIRNA AGAINST PHLDA3

(71) Applicants: Kyoto University, Kyoto (JP); TOHOKU UNIVERSITY, Sendai (JP); Rieko Ohki, Tokyo (JP); Kuraray Co., Ltd., Kurashiki (JP)

(72) Inventors: Shoichiro Sumi, Kyoto (JP); Rieko Ohki, Tokyo (JP); Naoaki Sakata, Sendai (JP)

(73) Assignees: Kyoto University, Kyoto (JP); Tohoku University, Sendai (JP); Rieko Ohki, Tokyo (JP); Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 15/313,020

(22) PCT Filed: May 22, 2015

(86) PCT No.: PCT/JP2015/064792
§ 371 (c)(1),
(2) Date: Nov. 21, 2016

(87) PCT Pub. No.: WO2015/178490
PCT Pub. Date: Nov. 26, 2015

(65) Prior Publication Data
US 2017/0157057 A1 Jun. 8, 2017

(30) Foreign Application Priority Data
May 23, 2014 (JP) .............................. JP2014-107529

(51) Int. Cl.
| | | |
|---|---|---|
| *A01N 63/00* | (2020.01) | |
| *A61K 9/48* | (2006.01) | |
| *A61K 31/7088* | (2006.01) | |
| *A61L 27/00* | (2006.01) | |
| *C12Q 1/02* | (2006.01) | |
| *A61K 45/00* | (2006.01) | |
| *A61K 48/00* | (2006.01) | |
| *A61K 31/7105* | (2006.01) | |
| *A61K 35/39* | (2015.01) | |
| *C12N 15/113* | (2010.01) | |
| *C12N 5/10* | (2006.01) | |

(52) U.S. Cl.
CPC ............ *A61K 9/48* (2013.01); *A61K 31/7088* (2013.01); *A61K 31/7105* (2013.01); *A61K 35/39* (2013.01); *A61K 45/00* (2013.01); *A61K 48/005* (2013.01); *A61L 27/00* (2013.01); *C12N 15/1136* (2013.01); *C12Q 1/02* (2013.01); *C12Q 1/025* (2013.01); *A61K 2121/00* (2013.01); *C12N 5/10* (2013.01)

(58) Field of Classification Search
CPC ....... A61K 9/48; A61K 31/7105; A61K 35/39

USPC ............................ 424/93.2, 93.21; 800/8–18
See application file for complete search history.

(56) References Cited

U.S. PATENT DOCUMENTS

| | | | |
|---|---|---|---|
| 2009/0181917 A1 | 7/2009 | Hua et al. | |
| 2014/0200393 A1* | 7/2014 | Khatib ................. | C12Q 1/6876 600/34 |
| 2016/0102366 A1* | 4/2016 | Abe .................... | A61K 31/5365 514/234.2 |

FOREIGN PATENT DOCUMENTS

| | | |
|---|---|---|
| WO | WO 2009/026317 A2 | 2/2009 |
| WO | WO 2010/087497 A1 | 8/2010 |

OTHER PUBLICATIONS

Jiao (Science, Mar. 2011, vol. 331, p. 1199-1203).*
Christgen (Lab. Investig. 2012, vol. 92, p. 1635-1647).*
Frank (PNAS, May 28, 2002, vol. 99, No. 11, p. 7490-7495).*
Saito (Annual Meeting of the Mol. Biol. Soc. Of Japan Program Yoshishu, Nov. 20, 2013, vol. 36, 1P-0874).*
Chen (Annual Meeting of the Mol. Biol. Soc. Of Japan Program Yoshishu, Nov. 20, 2013, vol. 36, 1P-0874).*
Ohki (PNAS, May 27, 2014, p. E2404-E2413).*
Skelin (Altex, 2010, vol. 27, p. 105-113).*
Ishihara (Diabetologia, 1993, vol. 36, p. 1139-1145).*
Frank (Mammalian Genome, 1999, No. 10, p. 1150-1159).*
Yoo (Pathology, 2011, vol. 43, No. 5, p. 510-511).*
Chen et al., "Elucidation of suppression mechanism of pancreatic endocrine tumor by PHLDA3 gene and MEN1 gene," The 36th Annual Meeting of the Molecular Biology Society of Japan Program Yoshishu, vol. 36, Abstract 1P-0875 (Dec. 3, 2013).
Frank et al., "Placental overgrowth in mice lacking the imprinted gene Ipl," *Proc. Natl. Acad. Sci. USA*, 99(11): 7490-7495 (2002).
Saito et al., "Akt suppressor gene PHLDA3 inhibits the growth of pancreatic β cells," The 36th Annual Meeting of the Molecular Biology Society of Japan Program Yoshishu, vol. 36, Abstract 1P-0874 (Dec. 3, 2013)
Japanese Patent Office, International Search Report in International Patent Application No. PCT/JP2015/064792 (dated Aug. 25, 2015).
Japanese Patent Office, International Preliminary Report on Patentability in International Patent Application No. PCT/JP2015/064792 (dated Jun. 29, 2016).
Aldibbiat et al., "Validation of Islet Transport from a Geographically Distant Isolation Center Enabling Equitable Access and National Health Service Funding of a Clinical Islet Transplant Program for England," *Cell Med.*, 21: 97-104 (2012).
Kuise et al., "Recent progress in pancreatic islet transplantation," *World J. Transplant.*, 1(1): 13-18 (2011).
Cheng et al., "Caspase-3 Gene Silencing for Inhibiting Apoptosis in Insulinoma Cells and Human Islets," *Mol. Pharm.*, 5(6): 1093-1102 (2008).

(Continued)

*Primary Examiner* — Michael C Wilson
(74) *Attorney, Agent, or Firm* — Leydig, Voit & Mayer, Ltd.

(57) ABSTRACT

The present invention provides a method for preparing a graft material containing organ or tissue cells, the cells including cells having inhibited PHLDA3 expression.

5 Claims, 13 Drawing Sheets

(56) References Cited

OTHER PUBLICATIONS

Kawase et al., "PH Domain-Only Protein PHLDA3 Is a p53-Regulated Repressor of Akt," *Cell*, 136(3): 535-550 (2009).
Sakata et al., "Encapsulated islets transplantation: Past, present and future," *World J. Gastrointest. Pathophysiol.*, 3(1): 19-26 (2012).
European Patent Office, Extended European Search Report in European Patent Application No. 15796080.8 (dated Nov. 7, 2017).

* cited by examiner

Red: Insulin
Green: Glucagon

METHOD OF ENCAPSULATING PANCREATIC ISLET CELLS INTRODUCED TO SIRNA AGAINST PHLDA3

CROSS-REFERENCE TO RELATED APPLICATIONS

This patent application is the U.S. national phase of International Patent Application No. PCT/JP2015/064792, filed on May 22, 2015, which claims the benefit of Japanese Patent Application No. 2014-107529, filed on May 23, 2014, the disclosures of which are incorporated herein by reference in their entireties for all purposes.

TECHNICAL FIELD

The present invention relates to a graft material and a method for preparing the graft material, and to an antidiabetic agent and a method for screening the antidiabetic agent.

The invention further relates to a transplantation efficiency enhancer.

BACKGROUND ART

Pancreatic islet transplantation has been performed as a treatment for diabetic patients because of less burden on the patient's body.

The biggest challenge in islet transplantation is to improve the engraftment rate in transplant outcomes, which remains low. It is impossible to obtain 100% of pancreatic islets by using current pancreatic islet isolation methods. Furthermore, since apoptosis of pancreatic islets is induced, for example, due to impairment in a pancreatic islet separation process and isolated pancreatic islets becoming avascular and being exposed to ischemia, the number of islet cells decreases after isolation, and insulin-secreting ability is significantly reduced. Further, after transplantation (according to current methods, direct intraportal administration), most of the transplanted pancreatic islets are lost early due to promoted ischemia at the graft site, which results from the influence of inflammatory reactants and cells caused by a blood coagulation reaction or the like and embolization of peripheral portal veins by pancreatic islet cells themselves. This phenomenon can be applied not only to pancreatic islets but also to all graft materials. Protecting graft materials and maintaining their functions have been desired.

Patent Literature (PTL 1) proposes inhibiting gene expression of EIF-5A1 by siRNA to protect pancreatic islets. However, the level and duration of the effect achieved by this method are both limited.

CITATION LIST

Patent Literature

PTL 1: WO2009/026317

SUMMARY OF INVENTION

Technical Problem

A primary object of the present invention is to inhibit apoptosis of graft cells during the process of preparing a graft material and to maintain the functions at high levels.

Solution to Problem

The present inventors conducted extensive research to achieve the above object. As a result, the inventors found that when the expression of PHLDA3 is inhibited, apoptosis of organ and tissue cells comprising pancreatic islet cells can be inhibited and an excellent graft material that maintains the functions can be provided.

The present invention provides the following graft materials and methods for preparing the graft materials, as well as the following antidiabetic agent, method for screening an antidiabetic agent, and transplantation efficiency enhancer.

Item 1. A method for preparing a graft material comprising organ or tissue cells, the cells comprising cells having inhibited PHLDA3 expression.

Item 2. The method according to item 1, wherein the graft material is a graft material of a kidney, liver, lung, heart, small intestine, pancreas, or pancreatic islets.

Item 3. The method according to item 1 or 2, wherein the cells forming the graft material maintain MEN1 function.

Item 4. The method according to any one of items 1 to 3, wherein the graft material is prepared under the action of a PHLDA3-expression or PHLDA3-function inhibitor.

Item 5. The method according to item 4, wherein siRNA of PHLDA3 is introduced as a PHLDA3-expression inhibitor into cells to prepare the graft material.

Item 6. The method according to any one of items 1 to 3, wherein the cells used to prepare the graft material have a genotype of PHLDA3 (−/−) or PHLDA3 (+/−).

Item 7. The method according to any one of items 1 to 6, wherein the cells are encapsulated in biocompatible capsule(s).

Item 8. A graft material comprising organ or tissue cells, the cells having a genotype of PHLDA3 (−/−) or PHLDA3 (+/−).

Item 9. The graft material according to item 8, which is derived from a non-human mammal.

Item 10. The graft material according to item 8 or 9, which comprises pancreatic islets.

Item 11. An antidiabetic agent comprising a PHLDA3 inhibitor.

Item 12. A method for screening an antidiabetic agent, comprising allowing each candidate substance to act on cells having a reporter-gene-containing expression vector introduced thereinto under the control of a PHLDA3 promoter, and selecting a candidate substance that reduces the amount of expression of the reporter gene.

Item 13. A transplantation efficiency enhancer comprising a PHLDA3-expression or PHLDA3-function inhibitor as an active ingredient.

Advantageous Effects of Invention

Fragile cells can be toughened by knockdown or knockout of PHLDA3 gene, which promotes apoptosis of graft material cells. In animals whose genotype of PHLDA3 gene is (−/−) or (+/−), hypertrophy and hyperplasia of pancreatic islets occur and pancreatic islets can be isolated with an extremely high yield.

Even when type 2 diabetes worsens and becomes insulin-dependent, inhibiting PHLDA3 revives the function of β cells and can treat diabetes. Immunosuppression or immunoisolation by encapsulation is preferably performed in order to avoid type 1 diabetes, in which autoimmunity is involved, or to avoid immune rejection after transplantation.

BRIEF DESCRIPTION OF DRAWINGS

FIG. 3B further 6+352 shows graphs of the area of pancreatic islet cells calculated for each type of mice.

FIG. 4A shows the effect of PHLDA3 expression on Akt activity in MIN6 cells. MIN6 cells were transduced with Ad-LacZ or Ad-PHLDA3 at the multiplicity of infection (MOI) of 35 and harvested 30 hours after the infection. Akt activation and phosphorylation of Akt downstream signaling molecules were analyzed by western blotting and quantified by normalization to total Akt levels (P-Akt) or by β-actin levels (P-p70 S6K, P-S6, P-Mdm2). FIGS. 4B and 4C show efficiency of siRNA inhibition of PHLDA3 expression in RIN cells. RIN cells were transfected with control or PHLDA3 siRNAs. PHLDA3 mRNA levels were analyzed by quantitative RT-PCR 31 hours after transfection and standardized against β-actin (FIG. 4B). Using cells subjected to γ-ray irradiation (20 Gy), as opposed to untreated cells, PHLDA3 protein levels were also determined by western blotting 48 hours after transfection (FIG. 4C). The γ-ray irradiated samples were included to help identify the band representing PHLDA3 protein. (PHLDA3 is induced by p53 activation.) FIG. 4D shows the effect of PHLDA3 expression on Akt activation in RIN cells. RIN cells were transfected as in FIG. 4B, and Akt activation was analyzed by western blotting 31 hours after transfection (left) and quantified by normalization to total Akt levels (right). FIG. 4E shows the effect of PHLDA3 expression on RIN cell proliferation. RIN cells were transfected as in FIG. 4B, labeled with BrdU for 3 hours, and harvested 28 hours after transfection. BrdU-positive cells were quantified by using a Ziva Ultrasensitive BrdU assay. FIG. 4F shows siRNA inhibition of PHLDA3 expression in primary islet cells. Isolated primary islet cells were transfected with control or PHLDA3 siRNA and harvested 30 hours after transfection. PHLDA3 mRAN levels were analyzed by quantitative RT-PCR as in FIG. 4B. FIG. 4G shows the effect of PHLDA3 expression on Akt activation in primary islet cells. Cells were transfected with siRNA as in FIG. 4F. Forty-eight hours after transfection, the cells were treated with glucose (30 mM) for 20 minutes. Levels of Akt activation were analyzed as in FIG. 4D. FIG. 4H shows the effect of PHLDA3 expression on primary islet cell proliferation. Cells were transfected as in FIG. 4F, labeled with BrdU for 4 hours, and harvested 30 hours after the transfection. BrdU-positive cells were analyzed as in FIG. 4E. FIGS. 4I and 4J show the effects of PHLDA3 expression on STZ-induced apoptosis of primary rat pancreatic islets. Isolated islets were pooled from three rats and transfected with control or PHLDA3 siRNA. Seventy-five hours after transfection, islets were treated with STZ (20 µg/mL) for 30 minutes. Islets were then cultured overnight and total RNAs were prepared. PHLDA3 expression was analyzed by quantitative RT-RCR as in FIG. 4B (FIG. 4I), or was subjected to TUNEL staining and analyzed by FACS (FIG. 4J).

DESCRIPTION OF EMBODIMENTS

Figure 1:
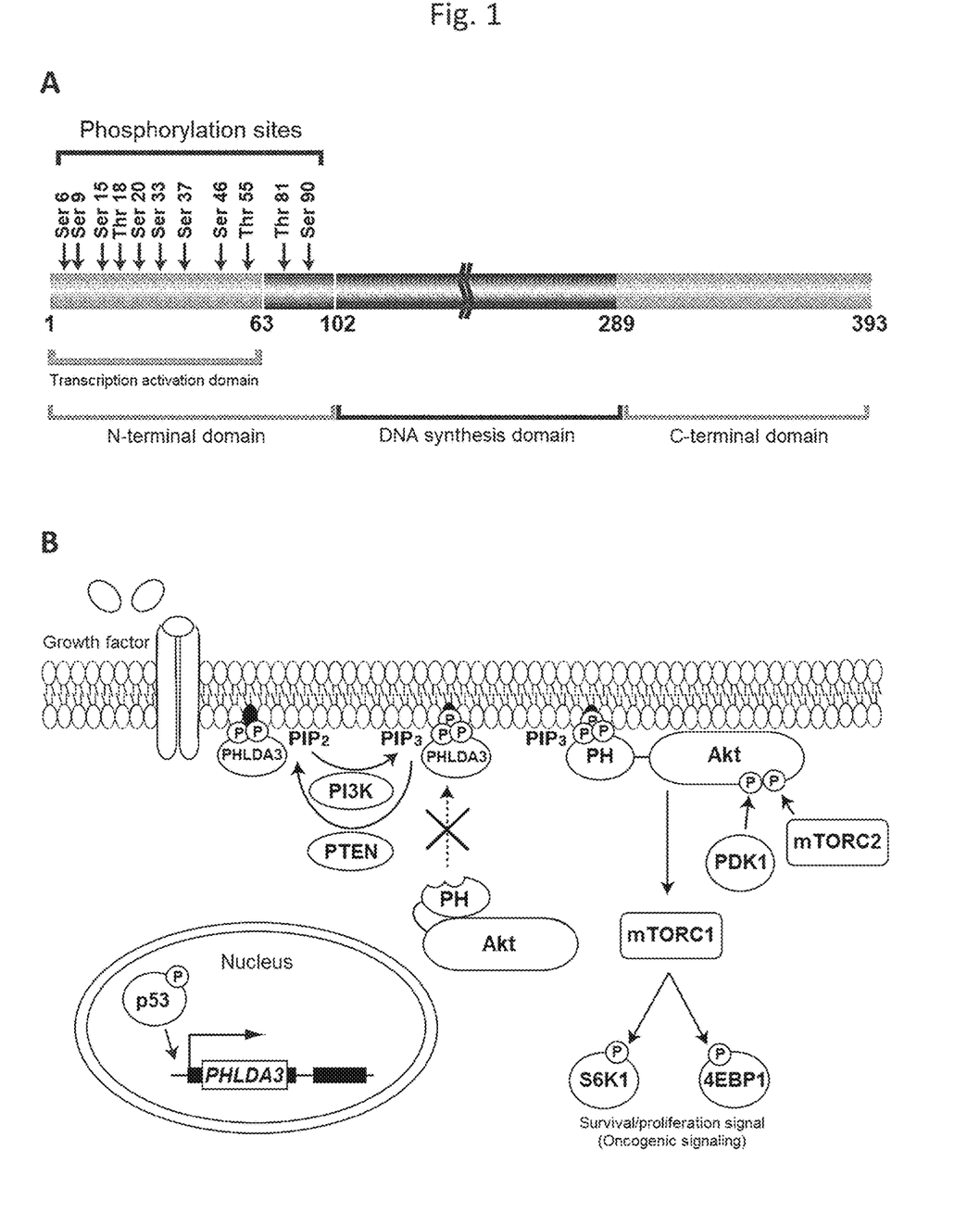
FIG. 1A shows the structure of p53 and phosphorylation sites in the N-terminal transcriptional activation domain.
FIG. 1B shows an Akt/mTOR pathway and an Akt inhibitory mechanism mediated by PHLDA3. PHLDA3 functions as if it were a dominant negative version of Akt and inhibits Akt activation.
FIG. 1C shows that oncogene Akt and antioncogene p53 control each other and form an Akt/p53 network. PHLDA3, which is a new target gene of p53, is also an antioncogene that inhibits the Akt pathway.
FIG. 1D shows the structure of PHLDA3.

PHLDA3 is a target gene of p53 (FIG. 1A) and encodes a protein consisting of 127 amino acids. PHLDA3 protein consists of a PH domain that serves for binding to $PIP_2$ or $PIP_3$. PHLDA3 protein competitively inhibits binding of Akt to $PIP_3$ and plays a role in an Akt activity suppressor pathway mediated by p53 (FIGS. 1B and 1C).

The accession numbers for the database of PHLDA3 used in the present invention are as follows: human PHLDA3 (Hs00385313_m1), mouse PHLDA3 (Mm00449846_m1), and rat PHLDA3 (Rn01483684_m1). The nucleotide sequences and amino acid sequences of PHLDA3 of other mammals than these are also similarly registered in a database.

PHLDA3 is an antioncogene. The present inventors confirmed that pancreatic neuroendocrine tumors (pNET) do not occur in PHLDA3 knockout mice and are formed only when deficiency or significant function reduction of both of PHLDA3 and MEN1 occurs simultaneously. Accordingly, neither an islet graft material in which PHLDA3 has been knocked down nor an islet graft material derived from a mammal in which PHLDA3 has been knocked out has the risk of developing cancer and can be suitably used as a graft material. The genotype of PHLDA3 of pancreatic islet cells may be a heterozygous genotype (+/−) or a homozygous mutant genotype (−/−). Hyperplasia of pancreatic islets and enhanced secretion of insulin can occur regardless of whether it is a heterozygous or homozygous mutant genotype. Pancreatic islets and islet cells having a heterozygous genotype (+/−) of PHLDA3 are preferable as graft materials because such pancreatic islets and islet cells have sufficiently high levels of islet cell functions and proliferation ability and also do not develop pancreatic neuroendocrine tumors (pNET) even when deficiency or significant function reduction of MEN1 gene occurs.

A reference (Mamm Genome, 1999, Dec. 10 (12): 1150-9) discloses that Tih1 (synonym of PHLDA3) is expressed in many organs and tissues. It is thus presumed that PHLDA3 functions not only in pancreatic islet cells but also in many organs and tissues. Accordingly, when the genotype of PHLDA3 is a heterozygous genotype (+/−) or a homozygous mutant genotype (−/−) or organs or tissues other than pancreatic islets are treated with a PHLDA3 protein inhibitor, apoptosis of organ or tissue cells for transplantation can be inhibited and function reduction during the preparation of a graft material can be reduced or inhibited. Examples of organs and tissues for transplantation include the kidney, liver, lungs, heart, small intestine, pancreas, pancreatic islets, and the like.

Since the PHLDA3-protein-expression or PHLDA3-protein-function inhibitor enhances the functions of graft cells and inhibits apoptosis of graft cells, the inhibitor is useful as a transplantation efficiency enhancer.

Preferably, the graft material is pancreatic islets. Therefore, the discussion below will focus on pancreatic islets. However, the discussion also applies to graft materials of other organs and tissues than pancreatic islets.

Pancreatic islet cells may be isolated from a pancreas for organ transplantation or may be prepared by inducing differentiation from stem cells capable of differentiating into islet cells, such as ES cells or iPS cells. PHLDA3 in ES cells or iPS cells may be knocked out, or PHLDA3 may be knocked down during the process of differentiation into islet cells. When a pancreatic islet graft material is prepared from a pancreas, PHLDA3 may be knocked down. Further, even when PHLDA3 is of a heterozygous genotype (+/−), hyperplasia of pancreatic islets occurs (FIG. 3A), and effects such as enhancement of pancreatic islet cell proliferation ability, inhibition of apoptosis, and enhancement of insulin-secreting ability are fully effective as achieved by knockdown. Although pancreatic islet graft materials can be prepared from a human pancreas, hypertrophied islets of non-human mammals (preferably pigs) in which the genotype of PHLDA 3 is a heterozygous genotype (+/−) or a homozygous mutant genotype (−/−) can be used as graft materials.

PHLDA3 may be knocked down by using RNAi, such as siRNA, shRNA, or microRNA, or by treating pancreatic islet cells with a PHLDA3 inhibitor.

Pancreatic islets can be isolated from a pancreas in a usual manner. For example, the islets can be isolated by treating a pancreas with a collagenase perfusion fluid or the like and centrifuging the treated material containing pancreatic islets. Knockdown of PHLDA3 may be performed after isolating pancreatic islets. siRNA of PHLDA3, etc., can be introduced into pancreatic islet cells, for example, by using a transfection reagent, such as Lipofectamine 2000. The pancreatic islet graft material is stored under refrigeration, optionally together with, for example, albumin.

As long as pancreatic islet cells are derived from a mammal, the origin of the cells is not particularly limited. Examples of mammals include humans, cows, horses, pigs, mice, rats, hamsters, goats, rabbits, dogs, cats, monkeys, and the like. For example, when pancreatic islets are to be transplanted to a human, human-derived islets are preferable. However, non-human, mammal-derived pancreatic islets, such as pig pancreatic islets, can also be transplanted.

The pancreatic islet graft material may consist only of pancreatic islet cells or may comprise pancreatic islet cells and a biocompatible material. Examples of the biocompatible material include collagen, adhesion molecules (laminin, fibronectin, nidogen), elastins, proteoglycans, hyaluronic acids, glycosaminoglycans, chitosan, alginates, biodegradable polymers (e.g., polylactic acid, polyglycolic acid, and polycaprolactam), and polyvinyl alcohol (PVA); cellulose derivatives such as hydroxypropylmethylcellulose (HPMC), sodium carboxymethylcellose (CMC-Na), and hydroxyethylcellulose (HEC); polysaccharides such as agarose, starch, dextran, and pullulan, and derivatives of polysaccharides; homopolymers such as carboxy vinyl polymers, polyethylene oxide, poly(meth)acrylamide, and poly(meth)acrylic acid, copolymers of these homopolymers with polysaccharide or the like, mixtures thereof, and copolymers with other monomers; polyion complex membranes of polyanion (e.g., alginic acid) with polycation (e.g., poly-L-lysine); and the like. The pancreatic islet graft material of the present invention may be encapsulated by a biocompatible material.

The present invention further provides a new method for screening an antidiabetic agent. Specifically, an expression vector ligated with a reporter gene under the control of a PHLDA3 promoter is introduced into cells under the control of a PHLDA3 promoter and the cells are treated with drug candidate substances. Drug candidate substances that decrease the amount of expression of the reporter gene, i.e., that inhibit PHLDA3 expression, are selected. The drug candidate substances that inhibit PHLDA3 expression are useful as antidiabetic agents because they enhance the proliferation of pancreatic islets and pancreatic islet cells and insulin production and secretion.

The cells used in the screening of the present invention may be prokaryotic cells such as bacteria, or eukaryotic cells such as yeast, plant cells, or animal cells. The cells are preferably eukaryotic cells, and more preferably animal cells. Animal cells may be cells of mammals, such as humans, mice, rats, rabbits, dogs, cats, monkeys, cows, horses, sheep, goats, or pigs; cells of birds such as chickens or ducks; cells of amphibians such as frogs; cells of reptiles such as newts; cells of fish or shellfish; or cells of insects. The cells are preferably mammal cells and most preferably human cells.

Examples of reporter genes include lacZ; fluorescent proteins such as luciferase (*Vargula hilgendorfii*, fireflies, *Renilla reniformis, Aequorea victoria*, and aequorin), GFP, YFP, BFP, CFP, DsRED, or RFP; chloramphenicol acetyltransferase; and the like.

In addition to a promoter, the cells may comprise an enhancer, transcriptional terminators, a start codon (ATG) in front of a protein-encoding gene, splicing signal for introns, and a stop codon.

Inhibition of PHLDA3 gene expression may be performed by using a nucleic acid, such as siRNA. Diabetes therapy may be performed by using a PHLDA3-protein-function inhibitor. Since PHLDA3 protein competitively inhibits binding of Akt and $PIP_3$, an antidiabetic agent can be obtained by screening the substance that promotes binding of Akt and $PIP_3$.

Pancreatic islets can be regenerated by administering a PHLDA3 protein inhibitor to a diabetic patient. Further, apoptosis of pancreatic islet cells can be inhibited by adding a PHLDA3 protein inhibitor to an organ preservation solution during the removal of the pancreas and allowing the inhibitor to continuously act during the isolation operation and up to transplantation.

EXAMPLES

The present invention is described in more detail with reference to the following representative Examples. However, the scope of the invention is not limited to the Examples below.

Example 1: Action of PHLDA3 on Pancreatic Islets

Figure 2:
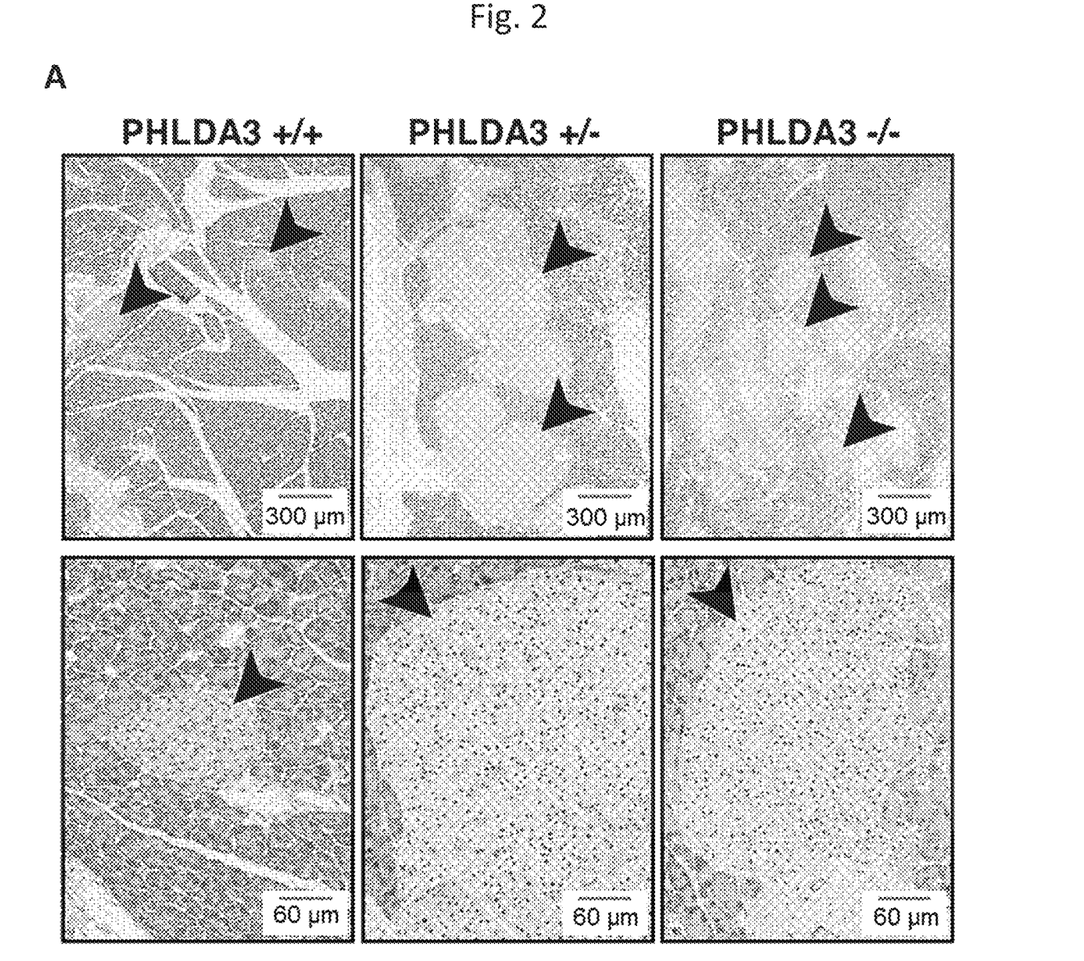
FIG. 2A shows hematoxylin eosin staining of pancreatic islets in PHLDA3 wild-type mice and PHLDA3-deficient mice.
FIG. 2B shows distribution of (insulin-positive) β cells and (glucagon-positive) α cells of pancreatic islets in PHLDA3 wild-type mice and PHLDA3-deficient mice.

PHLDA3 gene-deficient (+/−, −/−) mice were obtained in accordance with the following research paper: Frank D, et al., (2002), Placental overgrowth in mice lacking the imprinted gene Ipl. Proc Natl Acad Sci USA 99 (11): 7490-7495). Hyperplasia of pancreatic islets was observed in the PHLDA3 gene-deficient (+/−, −/−) mice (FIG. 2A).

Figure 3:
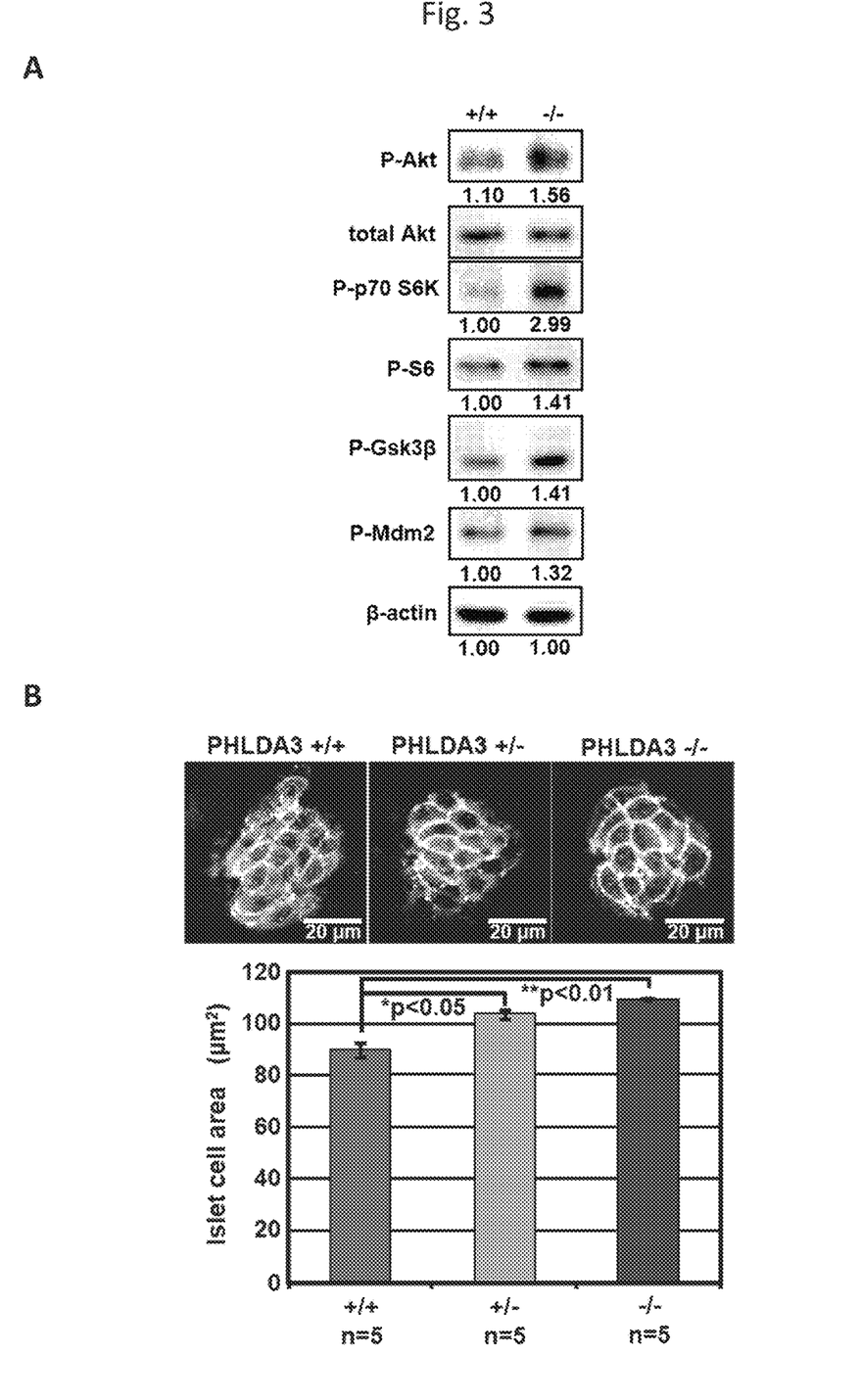
FIG. 3A shows the results of detecting Akt activity and Akt downstream signaling factors by western blotting. The activity of each factor is expressed in terms of numerical values relative to the activity of R-actin.
FIG. 3B shows pancreatic islets in PHLDA3 wild-type mice and PHLDA3-deficient mice.
FIG. 3C shows blood glucose concentrations in streptozotocin (STZ)-induced diabetes mice.
FIG. 3D shows the results of detecting (insulin-positive) β cells and (glucagon-positive) a cells of pancreatic islets in STZ-administered PHLDA3 wild-type mice and PHLDA3-deficient mice.

Accordingly, the present inventors examined what types of cells pancreatic islets in the state of hyperplasia are formed of. Pancreatic islets are mainly composed of β-cells, which produce insulin, and α-cells, which surround the β-cells and produce glucagon. Pancreatic islets were immunostained by using antibodies that recognize these hormones involved in glucose metabolism. It was found that abnormal proliferation of insulin-positive β-cells occurs in pancreatic islets of PHLDA3 gene-deficient mice, compared with the proliferation in wild-type mice (FIG. 2B). In pancreatic islets isolated from PHLDA3-deficient mice, phosphorylation of Akt and accompanying phosphorylation of factors downstream of Akt (phosphorylation of S6K and its substrate S6, Gsk3β, and Mdm2) were observed, and activation of an Akt/mTOR pathway was confirmed (FIG. 3A). Hypertrophy of pancreatic islet cells was observed in PHLDA3 gene-deficient mice (FIG. 3B). Further, the inventors administered streptozotocin (STZ) to PHLDA3 gene wild-type mice and PHLDA3 gene-deficient mice. Streptozotocin (STZ) induces apoptosis specifically to β cells, which produces insulin. Apoptosis of β cells in mice to which STZ was administered was detected by using an increase in blood glucose concentration as an indicator. The blood glucose concentration in PHLDA3 gene-deficient mice after STZ administration was significantly low compared with that in wild-type mice (FIG. 3C). A decrease in β cells was inhibited in PHLDA3 gene-deficient mice (FIG. 3D). The results show that PHLDA3 gene-deficient β cells are resistant to apoptosis.

These results reveal that inhibition of PHLDA3 protects pancreatic islets and can treat diabetes.

Further, it was observed that the effect on pancreatic islet cells in mice with partially deficient PHLDA3 gene (+/−) was similar to that in mice with completely deficient PHLDA3 gene (−/−). The results demonstrate that knockout of PHLDA3 is unnecessary and that slightly decreasing the amount of expression (knockdown) can treat diabetes without any risk of developing cancer.

Example 2: Knockdown Effect of Pancreatic Islet Cells by siRNA

Figure 4:
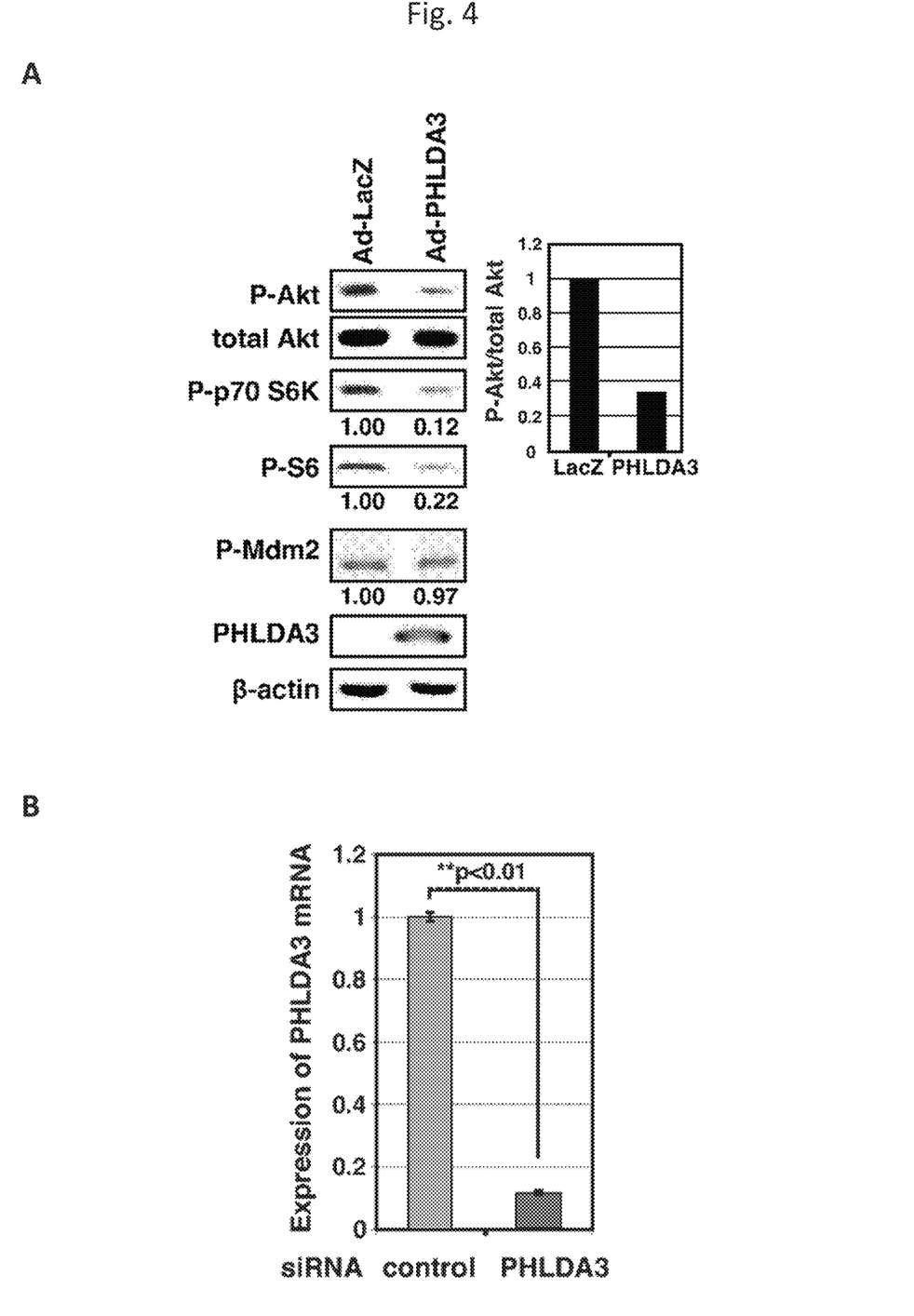
FIG. 4 shows the effects of PHLDA3 expression on Akt activity, cell proliferation and apoptosis in pancreatic islet cells.

Pancreatic NETs are derived from pancreatic islet endocrine cells. To analyze the functions of PHLDA3 in pancreatic islet β cells, examination was performed on RIN cells and MIN6 cells, which are cell lines derived from pancreatic β cells (FIGS. 4A to 4E). Although the RIN cells had detectable levels of PHLDA3 expression, MIN6 had only very low levels of PHLDA3 expression. The present inventors first used a gain-of-function approach and confirmed that PHLDA3 functions as a repressor of Akt in MIN6 cells. As shown in FIG. 4A, expression of PHLDA3 reduces Akt activation level and decreases phosphorylation of signaling molecules downstream of Akt. Similar results were also obtained by using PHLDA3−/−mouse embryonic fibroblasts. Next, the inventors knocked down PHLDA3 expression in RIN cells by using siRNA against PHLDA3 (FIGS. 4B and 4C) and confirmed increased Akt activation and cell proliferation (FIGS. 4D and 4E). The inventors obtained similar results by using normal primary rat islet cells. That is, knockdown of PHLDA3 expression brought about Akt activation and significant enhancement of cell proliferation in the presence or absence of glucose stimulation (FIGS. 4F to 4H). Next, the inventors analyzed the effects of PHLDA3 expression on apoptosis of pancreatic islet cells induced by streptozotocin (STZ), which has toxicity specific to insulin-producing β cells. Although inhibition of PHLDA3 expression in isolated rat pancreatic islets by siRNA was not so strong (FIG. 4I), this knockdown significantly reduced the number of apoptotic cells caused by STZ treatment (FIG. 4J). These results demonstrate that knockdown of PHLDA3 promoted pancreatic islet cell proliferation and inhibited apoptosis.

Example 3: Intrahepatic Transplantation of Pancreatic Islets

PHLDA3 gene is a p53 target gene. Carcinogenesis is inhibited by inhibiting oncogene Akt via PHLDA3 gene. A study found that PHLDA3 is involved in inhibiting the onset of pulmonary or pancreatic neuroendocrine tumors. The study revealed that inhibition of PHLDA3 causes hyperplasia of pancreatic islets of Langerhans in a pancreas (pancreatic islets: involved in controlling blood glucose) and pancreatic islets are larger than normal size, and the hyperplasia is such that only β cells (involved in insulin secretion) proliferate. The results suggest that engineering PHLDA3 can enhance the functions of pancreatic islets from normal levels, and may be applicable to cell therapy for diabetes intended to normalize blood glucose by transplanting pancreatic islets, i.e., islet transplantation. Accordingly, the inventors are in the process of examining whether enhanced islet transplantation effects can be obtained, as compared with islets of wild-type mice ("WT"), by isolating pancreatic islets from PHLDA3 knockout mice ("KO") and transplanting the obtained islets to diabetes mice.

Figure 5:
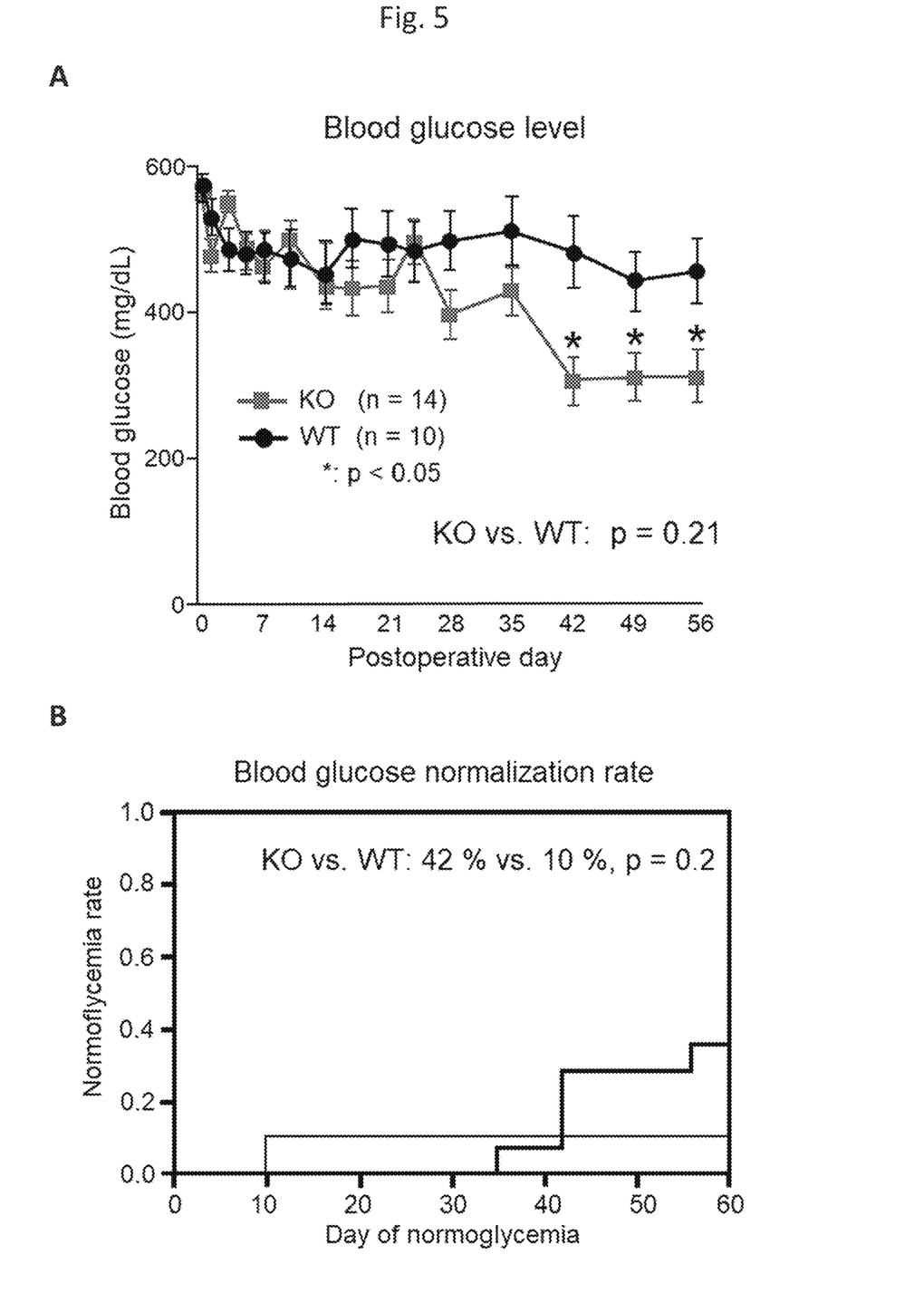
FIG. 5 shows intrahepatic islet transplantation data obtained by transplanting 150 IEQs. PHLDA3.

Therapeutic Effects of Intrahepatic Transplantation of PHLDA3 KO Pancreatic Islets The mainstream in clinical islet transplantation is intrahepatic transplantation in which pancreatic islets are engrafted in the liver via a portal vein. First, examination was performed by comparing therapeutic effects of PHLDA3 KO pancreatic islets in intrahepatic islet transplantation with those in the WT islet transplantation group. The number of pancreatic islets transplanted was 150. This is less than the minimum number of pancreatic islets (number of marginal donors) required for normalizing blood glucose. (In the inventors' study, the number of marginal donors required for intrahepatic islet transplantation is 200 to 300 pancreatic islets.) FIG. 5A shows blood glucose changes in diabetes mice after intrahepatic islet transplantation. In the assessment up to 56 days after the transplantation, the PHLDA3 KO islet transplantation group exhibited drastically improved blood glucose levels, in particular on day 42 or later after the transplantation, compared to the WT islet transplantation group. FIG. 5B shows that blood glucose was normalized (200 mg/dL or less) in many mice in the KO islet transplantation group. In the WT, 10% was normalized, whereas 42% was normalized in the KO. (There was no significant difference.) FIG. 5C shows blood glucose changes over time (glucose tolerance test) after intraperitoneal administration of a glucose solution. The product of blood glucose levels over time (blood-glucose change area: GTT-AUC), which was plotted on the ordinate, was significantly lower in the KO group. This shows that blood glucose change after glucose challenge in KO remained low compared to that in the WT. FIG. 5D shows serum insulin changes after transplantation. Although there is no significant difference, the KO had higher serum insulin levels than the WT. After the transplantation, rising in basal insulin level was observed, which is considered to lead to improvement of glucose tolerance in the KO group. FIG. 5E shows the results of excising the liver from mice 56 days after transplantation, observing specimens, and comparing the number of engrafted islets. Pancreatic islets were confirmed to be present in most of the samples in the KO group, whereas pancreatic islet engraftment was not observed in many samples in the WT group. Although a significant difference was not detected, engrafting of many islets tended to be observed in the KO group.

The above results show that in the intrahepatic transplantation system, excellent glucose tolerance improvement effects were provided in the KO group. Since intrahepatic transplantation is via the portal vein, i.e., intravascular transplantation, an acute coagulation reaction, which causes pancreatic islet loss, and ischemia, which occurs due to embolization of peripheral blood vessels by pancreatic islets themselves, are induced. Intrahepatic transplantation is thus considered to be conducted in a severe environment. The results of this experiment suggest that PHLDA3 KO pancreatic islets are tolerant to these conditions, i.e., acute stress. The results suggest the possibility that engineering of PHLDA3 may drastically improve the transplantation effect of intrahepatic transplantation of pancreatic islets.

INDUSTRIAL APPLICABILITY

The number of type 1 diabetes patients by age group is such that the number of child patients with type 1 diabetes is rapidly increasing worldwide, and the global number of child patients 15 or younger with type 1 diabetes is 495,100, with the number of the patients age 15 to 25 even higher, and the total number of patients 25 or older is several million. Blood glucose control is relatively easy for young people. However, control is difficult for people in their thirties or older, and many patients desire to have islet transplantation. At present, several tens of patients annually receive islet transplantation worldwide.

Pancreatic islets having inhibited PHLDA3 expression and pancreatic islets obtained from PHLDA3 gene-deficient pigs have a high engraftment rate after transplantation and are highly effective as diabetes therapy. Further, the development of a PHLDA3 small molecular inhibitor enables pancreatic islet toughening, amplification, and improved transplant outcomes; and functional reduction of pancreatic islet cells in type 2 diabetes can be delayed or inhibited.

The invention claimed is:

1. A method of encapsulating pancreatic islet cells comprising (i) introducing siRNA against PHLDA3 into isolated mammalian pancreatic islet cells such that the cells exhibit decreased PHLDA3 expression as compared to isolated mammalian pancreatic islet cells not introduced to the siRNA; and (ii) encapsulating the pancreatic islet cells that exhibit decreased PHLDA3 expression obtained in step (i).

2. The method according to claim 1, wherein the pancreatic islet cells maintain MEN1 function.

3. The method according to claim 1, wherein the mammalian pancreatic islet cells are mouse pancreatic islet cells.

4. The method according to claim 1, wherein the mammalian pancreatic islet cells are rat pancreatic islet cells.

5. The method according to claim 1, wherein the mammalian pancreatic islet cells are human pancreatic islet cells.

* * * * *